US006808879B1

(12) United States Patent
Guillot et al.

(10) Patent No.: US 6,808,879 B1
(45) Date of Patent: Oct. 26, 2004

(54) MEANS FOR QUALITATIVE AND QUANTITATIVE ANALYSIS OF MICROBIAL POPULATIONS POTENTIALLY PRESENT IN A SAMPLE

(75) Inventors: Emmanuelle Guillot, Le Pecq (FR); Vincent Urbain, Le Vésinet (FR); Jacques Manem, Le Buisson de Cadouin (FR); Bruce E. Rittmann, Evanston, IL (US); David A. Stahl, Evanston, IL (US); Jodi Flax, Chicago, IL (US); Michaël Wagner, Munich (DE)

(73) Assignees: Suez Lyonnaise Des Eaux, Naterre Cedex (FR); Northwestern University, Evanston, IL (US)

( * ) Notice: Subject to any disclaimer, the term of this patent is extended or adjusted under 35 U.S.C. 154(b) by 0 days.

(21) Appl. No.: 09/529,217
(22) PCT Filed: Oct. 2, 1998
(86) PCT No.: PCT/EP98/06286

§ 371 (c)(1),
(2), (4) Date: Jun. 5, 2000

(87) PCT Pub. No.: WO99/18234

PCT Pub. Date: Apr. 15, 1999

(30) Foreign Application Priority Data

Oct. 8, 1997 (FR) ............................................ 97 12552

(51) Int. Cl.⁷ ............................ C12P 1/68; C12P 19/34; C07H 21/04
(52) U.S. Cl. ......................... 435/6; 435/91.1; 435/91.2; 536/23.1; 536/24.32
(58) Field of Search .......................... 435/6, 91.1, 91.2; 536/23.1, 24.3, 24.32

(56) References Cited

U.S. PATENT DOCUMENTS 5,403,711 A * 4/1995 Walder et al.
5,426,025 A   6/1995 Reeves et al. ................. 435/6
5,538,871 A * 7/1996 Nuovo et al.
5,691,146 A * 11/1997 Mayrand

FOREIGN PATENT DOCUMENTS

WO    WO 88/03975    6/1988
WO    WO 91/00926    1/1991
WO    WO 96/19585    6/1996
WO       97/27328   * 7/1997

OTHER PUBLICATIONS

Journal of Experimental Marine—Burton, R.S., 1996.*
XP-002068767, Wagner et al, In situ Identification of Ammonia-oxidizing Bacteria, *System. Appl. Microbiol.* 18, 251–264 (1995).
XP-002068768, De Los Reyes et al, Group–Specific Small–Subunit rRNA Hydridication Probes to Characterize Filamentous Foaming in Activated Sludge Systems, *Applied and Enviromental Microbiology*, Mar. 1997, pp. 1107–1117.
Manz et al, In Situ Characterization of the Microbial Consortia Active in Two Wastewater Treatment Plants, *2406 Water Research*, 28 (1994), Aug., No. 8, pp. 1715–1723.
XP-002068769, Wagner et al, Probing Activated Sludge with Oligonucleotides Specific for Proteobacteria: Inadequacy of Culture–Dependent Methods for Describing Microbial Community Structure, *Applied and Environmental Microbiology*, May 1993, pp. 1520–1525.
XP-002097846, Wagner et al, Development of an rRNA–Targeted Oligonucleotide Probe Specific for the Genus *Acinetobacter* and Its Application for In Situ Monitoring in Activated Sludge, *Applied and Environmental Microbiology*, Mar. 1994, pp. 792–800.
XP-002068770, Mobarry et al, Phylogeneric Probes for Analyzing Abundance and Spatial Organization of Nitrifying Bacteria, *Applied and Environmental Microbiology*, Jun. 1996, pp. 2156–2162 + Errata sheet.
Lemmer et al, Denitrification in a Methanol–Fed Fixed–Bed Reactor, Part 2: Composition and Ecology of the Bacterial Community in the Biofilms, *Wat. Res.*, vol. 31, No. 8, pp. 1903–1908, 1997.

* cited by examiner

*Primary Examiner*—Jehanne Sitton
(74) *Attorney, Agent, or Firm*—Connolly Bove Lodge & Hutz LLP

(57) ABSTRACT

This invention relates to means of qualitative and quantitative analysis of microbial populations potentially present in a sample. These means notably comprise the use of at least one RNA-targeted oligonucleotide probe for in situ hybridization in whole cells; followed by the extraction of those probes which have become hybridized by separation from their target and elution from the microbial cells; as well as the detection and measurement of said extracted probes.

30 Claims, No Drawings

MEANS FOR QUALITATIVE AND QUANTITATIVE ANALYSIS OF MICROBIAL POPULATIONS POTENTIALLY PRESENT IN A SAMPLE

FIELD OF INVENTION

This invention may be generally described as a means of qualitative and quantitative analysis of microbial populations potentially present in a sample. More specifically, it relates to a means of qualitative and quantitative analysis using RNA targeted oligonucleotide probes.

BACKGROUND

The analysis of microbial populations potentially present is required for many types of solid and fluid samples. Some notable examples are those samples obtained from a natural or biological environment such as natural water or hot springs; samples taken from humans or animals such as blood, urine, vaginal and intestinal flora; and samples from urban, agricultural and industrial environments such as food products, industrial water, industrial effluents, municipal wastewater, industrial sludge, fermentation media, aerosols, filters or air from air conditioning systems.

Various laboratory techniques have been developed for the qualitative and quantitative analysis of microbial populations potentially present in a given sample.

One familiar technique involves a count of the microorganisms that develop after the sample (or an extract thereof) is cultured on various selective nutrient media under standard conditions. This technique is simple but entails significant risks of errors and artifacts (low specificity of morphological criteria, inability to detect viable but non-culturable microorganisms, inability to detect slow-growing microorganisms, need to maintain viability of bacteria between collection and enumeration). Moreover, this technique generally requires longer than 24 hours to yield results.

A second technique, which entails the measurement of the activity of one or more enzymes, allows a rapid quantification of populations of living microorganisms (culturable microorganisms and/or microorganisms in a viable but non-culturable form). This technique can be used, in particular, to monitor a set of populations, but does not achieve very high levels of specificity or sensitivity.

A third technique using immunological probes often requires a growth step and thus requires longer than 24 hours to yield results. Moreover, it frequently lacks both sensitivity and specificity (misidentification may occur due to cross-reactions).

The most recent techniques are based on the use of specific DNA probes, which are generally labeled to permit detection after hybridization with their targets. Two main categories of oligonucleotide probes have been developed: those that target DNA and those that target RNA (ribosomal RNA or messager RNA).

DNA-targeted probes, although potentially highly specific, have the drawback of low sensitivity due to the few copies of the target DNA genes in each microbial cell. Although the use of PCR (polymerase chain reaction) to amplify the target DNA sequences before detection can compensate for the lack of sensitivity of the DNA probes, it has several drawbacks of its own: for example, the presence of inhibitors can lead to false-negative reactions, while carry-over or similar contamination can lead to false-positive reactions. In contrast, the use of RNA-targeted probes prevents from such drawbacks. In particular, because of the large number of copies of rRNA that occur naturally in a microorganism (actively growing cells may contain $10^4$ ribosomes, each a potential probe target), the use of rRNA-targeted probes does not require the amplification step, thereby overcoming the constraints and artifacts associated therewith. The advantage of targeting rRNA is that about 85–90 percent of the total RNA in a typical cell is rRNA.

The hybridization of RNA-targeted probes can be achieved either after cell lysis, extraction and purification of the total nucleic acids of the sample, or in situ on whole cells, generally after fixation (permeabilization) of the membrane (or wall) of the microorganisms potentially present in the sample.

However, cell lysis and the ensuing extraction and purification of the nucleic acids particularly total RNA, are delicate and time-consuming manipulations that require costly apparatus, trained personnel and strict experimental conditions, notably the prevention of contamination by nucleases during the procedure. This technique further implies the use of a solid support, such as a nylon membrane, onto which the purified nucleic acids are immobilized in such a way one can discriminate between them (e.g. dot-blot, slot-blot). It most generally also implies the use of radioactive probe labels, the handling of which requires special care. The cell lysis technique for RNA hybrididization is therefore ill-suited to use in routine analysis either in industry or in biological laboratories.

In situ hybridization in whole cells overcomes the need for preliminary extraction of the target nucleic acids by cellular lysis with all its associated disadvantages. The FISH (Fluorescent In Situ Hybridization) process, which employs fluorescence-labeled rRNA probes, is one existing in situ technique. This type of technique, generally involving fluorescence microscopy, provides a fast and sensitive qualitative analysis on many types of sample. Today, rRNA-targeted probes thus hybridized in situ with their target within whole cells can be quantified directly on the sample (flow cytometry, microscopy), although the method is not entirely satisfactory: quantification directly on the sample is technically costly, time-consuming, requires trained personnel and does not permit an accurate quantification of hybridized probes when the sample is complex and non-uniform (e.g. floc or aggregates formed by filamentous bacteria in sewage treatment sludge; samples containing naturally fluorescent microorganisms). As a result, the technique of in situ hybridization in whole cells using fluorescence-labeled oligonucleotide probes has, to date, remained an essentially qualitative technique that does not provide reliable quantitative results.

To meet the need for industrial-caliber performance on samples that can be complex and/or non-uniform, this invention provides a means for analyzing, both qualitatively and quantitatively, the microbial populations potentially present in a biological sample, said means overcoming the disadvantages of prior art techniques

SUMMARY OF THE INVENTION

The object of this invention is, therefore, a method of qualitative and quantitative analysis of the microbial population(s) potentially present in a sample, characterized in that it comprises:
 contacting the microorganisms potentially present in said sample with at least one RNA-targeted oligonucleotide probe, hereafter called specific probe, able to target a desired microbiological population, under conditions favourable to in situ hybridization in whole cells, extracting, by separation from their target and elution outside said cells, those probes which have become hybridized, detecting the extracted probes and measuring the amount thereof or their respective amounts.

The present invention thus advantageously enables the extraction of said probes without destruction of said cells.

DETAILED DESCRIPTION OF THE INVENTION

As used herein, the term "microbiological population" (or "microbiological domain") means the set of microorganisms that a given probe is able to recognize by recognition of an RNA target sequence present in each member of said set. The approach is based on RNA target sequence present in each member of said set. The approach is based on oligonucleotide hybridization probes complementary to RNA sequences that are diagnostic for selected phylogenetic groups which correspond, to varying degrees, to a target region typical of a type of a microorganism or a whole group of microorganisms. Any probes enabling said contacting step is appropriate for the implementation of the method according to the invention. The choice of the specific probe(s) is directly related to the analysis desired for said sample. Probes can e.g. be composed of oligonucleotide sequences that can distinguish between the primary kingdoms (eukaryotes, eubacteria, archaebacteria) and between closely related organisms (the group of Ammonia-oxidizing β-Proteobacteria, the genus Nitrobacter or Acinetobacter or the species *Fibrobacter intestinalis*, the species *Escherichia Coli*). Probes with finer phylogenetic resolution can be derived by using the existing collections of RNA sequences. Many examples of such RNA-targeted probes are described in the prior art such as patents or patent applications, scientific publications e.g. Los Reyes et al. 1997, Appli. Environ. Microbiol. Vol. 63 No. 3 p.1107–1117; Mobarry et al. 1996, Appli. Environ. Microbiol. Vol. 62 No. 6 p.2156–2162; Wagner et al. 1994, Appli. Environ. Microbiol. Vol. 60 No. 3 p.792–800; Kane et al. Appli. Environ. Microbiol. Vol. 59 No. 3 p.682–686. Other examples of such probes can also be designed by the person skilled in the art. Advantageously probes are those which target ribosomal RNA (rRNA). Examples of such advantageous probes include Nb 1000 (SEQ ID No. 1) and Nso 1225 (SEQ ID No. 2).

The method of the invention gives particularly accurate quantitative results when the cell numbers in said sample are equal to or greater than approximately $10^3$ or $10^4$ cells per ml. If desired, the microorganism concentration of a liquid sample can be increased by filtration or any other technique prior to implementing the method of the invention.

In a preferred arrangement of the invention, said microorganisms potentially present in the sample are also contacted with at least one probe, hereafter called "universal probe", serving to normalize the results obtained with probes targeting specific phylogenetic groups of microorganisms ("specific probes"). The amount of a specific probe in said sample may then be expressed as a ratio of the amount of said universal probe. Such an universal probe may thus enable the expression of e.g. the specific target rRNA as a percentage of the total rRNA. Examples of such "universal probes" include probes specific for any microorganism, or probes specific for bacteria, or for eukaryotes. Such "universal probes" are well-known in the art and any of them can be used as long as it enables said contacting step, and allows the desired "specific probe" normalization. Such a "universal probe" is used in the method according to the invention similarly as a "specific probe", and accordingly is advantageously a rRNA-targeted probe.

It may be advantageous to extract the microorganisms potentially present in said sample therefrom, in particular by centrifugation, prior to proceeding with any step of the method of the invention. One reason to proceed in this manner is to remove the background noise that a sample of complex composition can generate. Another reason may be to place into solution the microorganisms potentially present in a solid, gazeous or viscous sample.

According to one embodiment of the invention, said contacting step is performed after the cells are made to undergo a fixation step (or permeabilization step) essential for maintaining their morphological integrity, and which makes the microorganisms potentially present in said sample permeable to short oligonucleotide probes (ca 15–25 nucleotides). This fixation step allows the probes to penetrate inside the microbial cells without affecting the integrity thereof, thereby attaining their target or targets in situ. Where applicable, said sample is homogenized prior to said fixation step in order for said at least one probe to have access to all microbial populations potentially present in the sample.

Said fixation is advantageously achieved by incubating said cells in a paraformaldehyde solution that is less than 10%, preferably around 4%, for 3 to 12 hours at 4° C. This fixation procedure is more particularly adapted to Gram-negative bacterias. For certain Gram-positive bacterias, said fixation step may be achieved by incubating said cells in a 100% ethanol solution.

Following fixation, said cells can be recovered by e.g. centrifugation and stored until use at −20° C. in a buffered solution at a pH of about 7 (PBS buffer, for example) containing approximately 60% ethanol.

In a preferred arrangement of this embodiment of the invention, said fixation is followed by a dehydration step (or drying step) prior to said contacting phase. Said dehydration step can thus be carried out by placing said sample in contact with at least one ethanol solution, preferably with a series of ethanol solutions of increasing concentration, for example by placing the sample in a 70%, 80% and then 95% ethanol solution.

Advantageously, said contacting phase is performed by placing the sample in contact with said at least one probe in the presence of a solution hereafter called "hybridization solution", which comprises a denaturing agent such as sodium dodecyl sulfate (SDS) at a concentration in a 0.001–0.1% range, preferably on the order of 0.01%; Tris-HCl, pH of about 8 at a concentration in a 0.001–0.1M range, preferably on the order of 0.02M; and a salt such as sodium chloride at a concentration in a 0.1–1.5M range, preferably on the order of 0.9M. Such a contacting is advantageously performed for an incubation time comprised between about 10 minutes and about 2 hours, and at an hybridization temperature, which is preferably the optimal temperature. For each oligonucleotide probe, the hybridization conditions (temperature; concentration of salts and denaturing agents) can be indeed optimized so as to improve the specificity of the oligonucleotide probe for the corresponding RNA sequences found in the target cells. When a plurality of oligonucleotide probes is used simultaneously, these hybridization conditions can be chosen so as to take into account the optimal conditions peculiar to every probe.

It is very advantageous for the extraction of said at least one probe to be performed following the removal of excess and unbound probe or of non-specifically associated probe material placed in contact, notably by washing with a solution hereafter called "wash solution". Such a "wash solution" advantageously comprises a denaturing agent such as sodium dodecyl sulfate (SDS) at a concentration in a 0.001–0.1% range, preferably on the order of 0.02%; tris-HCl pH of about 8 at a concentration in a 0.001–0.1M range, preferably on the order of 0.02M, and a salt such as sodium chloride at a concentration in a 0.01–0.9M range, preferably on the order of 0.1M. The formulation of the <<wash solution>> (e.g. salt and denaturant nature and/or concentration) is adjusted so as to achieve the appropriate stringency; i.e. the stringency necessary to the removal of non-specifically associated probe. Thanks to such a washing step, the extraction step will be performed only on those probes which have become effectively hybridized to the desired target(s).

According to a preferred embodiment of the invention, said extraction is performed by placing the microorganisms potentially present under conditions to denature enabling the denaturation of every probe specifically associated with its target sequence, notably in the presence of a probe-target denaturing agent such as one that will separate duplex DNA/DNA or DNA/RNA, and in particular the probe—target duplex under consideration, and at a temperature higher than the melting temperature of the probe under consideration, notably at a temperature of about 100° C. According to a particularly preferred embodiment of the invention, said denaturing agent is formamide. Said extraction is then performed by incubating said microorganisms in formamide at 100° C. for 10 minutes using a controlled temperature incubator. The supernatant may then be recovered for quantification, e.g. by centrifugation. To improve detection, said extracted probes can be concentrated notably using a Speed-Vac® prior to measuring the corresponding amount of each probe.

The detection of a target-hybridized probe and the measurement of its amount thus give a qualitative and quantitative analysis of the set of target-microorganisms present in the sample. It is advantageous to perform said detection and amount measurement of the extracted probes by detection and amount measurement of a label associated with or incorporated into each of the contacted probes, such as a radioactive ($^{32}$P, $^{35}$S, $^{125}$I), chemiluminescent or fluorescent label. The respective amounts of probes are then measured by quantitation of the corresponding label. It is particularly advantageous to use a fluorescent label, notably fluorescein which can be easily quantified using a fluorescence spectrophotometer.

Different probes, e.g. specific probe(s) and/or universal probe(s), can be placed in separate samples, or in the same sample. In the latter case, it is possible to distinguish each probe used from the others during the detection step, for example by giving to each one its own specific label (e.g. different fluorochromes).

The method of the invention can be applied to a variety of samples. Samples for which an analysis using the method of the invention is of particular interest include those taken from fluids such as natural water, industrial water, industrial effluents, municipal wastewater, industrial sludge, thermal mud, food liquid or gel, fermentation medium, air, gas, aerosol; samples from a building ventilation duct, air conditioning duct; samples from edible solid, soil; samples from medical apparatus; human or animal samples such as blood, urine, vaginal or intestinal flora.

The method of the invention utilizes neither microbiological culture, nor microscopy, nor an in vitro amplification step (like PCR) and does not require any cell lysis step. It is reproducible, simple, fast (less than 3 hours), low-cost and does not require specially trained personnel. The method of the invention offers the additional advantage of being easy to automate. The method of the invention notably provides a qualitative and quantitative measurement of the microbiological or sanitary status of said sample and, consequently, of the product from which said sample is taken. The method of the invention can therefore advantageously be combined with an alarm function relating to the quality, safety and/or sanitary monitoring of the product from which the sample is taken, notably as part of an industrial production line.

When the threshold value or set point is exceeded, the method of the invention permits the corresponding quality, safety and/or sanitary alarm to be triggered. It also permits the automatic or feedback control of a microbiological removal or enrichment process.

This invention also relates to the application of said method to in vitro diagnostics of infectious diseases.

Beyond applications of the "status or condition measurement" and "alarm" types, this invention relates in particular to the application of said method for the automatic or feedback control of microbiological processes such as methane fermentation of liquid manure, treatment of organic effluents, sewage treatment processes such as activated sludge treatment; or to the automatic or feedback control of a process aimed at removing or preventing the growth of microorganisms.

Thus, the method of the invention may be advantageously applied to the detection of foam formation during the implementation of activated sludge processes and/or to the feedback control of a process aimed at removing or preventing the development of such foams.

Other features and advantages of the invention will further become apparent in the following exemplary embodiments, which are given for illustrative and non-limiting purposes.

EXAMPLE 1

Qualitative and Quantitative Analysis of a Sample of Sewage Treatment Reactor Effluent a) Fixation Step Samples of effluent from sewage treatment activated sludge reactors are mixed and then washed three times using a phosphate buffer solution (PBS phosphate-buffered saline) at pH 7. The sample is then incorporated into three volumes of a 4% paraformaldehyde solution and incubated for 3 to 12 hours at 4° C. Following centrifugation the supernatant is removed and the sample is again mixed with a phosphate-buffered saline solution (PBS) at pH 7. An equal volume of ethanol is added and the sample can be stored at −20° C. until use.

b) Dehydration Step

The fixed sample is centrifuged after adding 1 ml of 70% ethanol over the residue and resuspending the cells. The mixture is centrifuged for 5 minutes then the supernatant is removed. This procedure is repeated with 80% ethanol and then again using 95% ethanol.

c) Hybridization Step

A water bath is prepared at the hybridization temperature required by the probe being used (the temperature depends on the length and sequence of the probe). In the example reported here, the following probes were used:

Probe Nb 1000 specific to the Nitrobacter genus, with sequence SEQ ID No. 1: 5' TGCGACCGGTCATGG 3'

Probe Nso 1225, specific to Ammonia-oxidizing β proteobacteria, with sequence SEQ ID No. 2: 5' CGCCATTGTATTACGTGTGA 3'

Probe S Univ-1390, a universal probe for any microorganism, with sequence SEQ ID No. 3: 5' GACGGGCGGTGTGTACAA 3', and Probe S Bac338, specific for bacteria, with sequence SEQ ID No. 4: 5' GCTGCCTCCCGTAGGAGT 3'.

These probes were synthesized, purified by High Performance Liquid Chromatography (HPLC), then fluorescein-labeled at the 5' end. They are available from Operon Technologies of Alameda, Calif. (USA) or, in France, from the Genset company based in Paris (among others).

The cells obtained from the dehydration step are resuspended in 400 μL of a hybridization solution comprising (for 10 mL): NaCl 5M 1.8 mL; Tris-HCl 1M 200 μL; SDS (sodium dodecyl sulfate) 5 μL; distilled excipient water 8 mL, for ten mL. After each probe is labeled by a fluorochrome, the necessary quantity of each probe is added (here, 1.5 nanomoles). The cells in the hybridization solution in contact with the probes are incubated for 10 minutes to 2 hours at the hybridization temperature. The hybridization samples are centrifuged and supernatants are removed.

d) Washing Step

Following hybridization, the cells are washed twice for 15 minutes each time at the hybridization temperature, in a buffered washing solution comprising, for 50 mL, NaCl 5M 1 mL; Tris-Hcl 1 M 9 mL; SDS 20% 50 μL. The formulation of the <<washing solution>> (e.g. salt and denaturant) is adjusted according to need of achieving appropriate stringency, i.e. removal of non-specifically associated probe.

e) Extraction of the Fluorescence by Elution

300 μL of formamide heated to 100° C. is added to the samples obtained from the washing step, and the residue is gently resuspended. Each tube is placed in 100° C. for 10 minutes, preferably using a controlled temperature incubator. Centrifuge for 10 minutes. The supernatant is recovered and stored in the dark until it can be analyzed by fluorescence spectroscopy. The fluorescence is quantified using a spectrofluorometer. The amounts measured in probes Nb1000 and Nso 1225 correspond to the relative amounts of Nitrobacter bacteria and Ammonia-oxidizing β proteobacteria contained in the sample. These amounts are compared with those measured for universal probe S Univ-1390 and bacteria probe S Bac 338.

This gives a percentage ratio (the relative proportion) of the microorganisms contained in the sample, which are respectively Nitrobacter and Ammonia-oxidizing β proteobacteria.

It is understood that this invention is not limited to the embodiments described and illustrated herein, but covers all variants thereof.

What is claimed is:

1. A method of qualitative and quantitative analysis of microbial population(s) comprising:
providing a sample containing microorganisms,
contacting the microorganisms present in the sample with at least one specific probe to form a sample with a probe-target complex in situ hybridization in whole cells, wherein the specific probe recognizes a RNA target sequence,
contacting the sample with the probe target complex with a wash solution to remove excess specific probes or non-specific probes from the sample with the probe target complex thereby providing a washed sample,
adding a denaturing agent to the washed sample to extract the specific probes from the probe-target complex, and
detecting the extracted probes and measuring the amount thereof or their respective amounts to provide the qualitative and quantitative analysis of the microorganisms in the sample.

2. A method according to claim 1, wherein said at least one specific probe is chosen among the group consisting of SEQ ID NO: 1 and SEQ ID NO: 2.

3. A method according to claim 1, further comprising contacting said microorganisms present in said sample with an universal probe to normalize results.

4. A method according to claim 3, wherein said universal probe is chosen among the group consisting of SEQ ID NO: 3 and SEQ ID NO: 4.

5. A method according to claim 3 wherein said specific or said universal probe is a mRNA-targeted probe.

6. A method according to claim 1, further comprising extracting said microorganisms in said sample by centrifugation.

7. A method according to claim 1, further comprising fixing of said whole cells prior to contacting the microorganisms with the at least one specific probe.

8. A method according to claim 7, wherein fixation of the cells is achieved by incubation of the cells in a fixation solution of less than 10% paraformaldehyde for 3 to 12 hours at 4° C.

9. A method according to claim 7, wherein said fixation is followed by a dehydration step, prior to said contacting the microorganisms with the at least one specific probe.

10. A method according to claim 9, wherein the dehydration is performed by placing said sample in contact with at least one ethanol solution.

11. A method according to claim 1, wherein said contacting the microorganisms with the at least one specific probe includes placing said sample in contact with said specific probe in the presence of a hybridization solution comprising a denaturing agent at a concentration of from 0.001% to 0.1%, Tris-HCl with a pH of about 8 at a concentration of from 0.001 M to 0.1 M, and a salt at a concentration of from 0.1 M to 1.5 M.

12. A method according to claim 1, wherein contacting the microorganisms with the at least one specific probe includes an incubation time of about 10 minutes to about 2 hours, and at an optimal hybridization temperature.

13. A method according to claim 1, wherein the wash solution comprises a salt at concentrations appropriate for achieving the stringency necessary for the removal of non-specifically associated probe.

14. A method according to claim 1, wherein extracting of the hybridized probes includes extracting at a temperature higher than the melting temperature of the specific probe under consideration.

15. A method according to claim 14, wherein extracting of the hybridized probes includes adding formamide to the washed sample.

16. A method according to claim 1, wherein said extracted probes are concentrated prior to the measurement of the amount thereof or of their respective amounts.

17. A method according to claim 1, wherein said detecting and measuring the amount of the extracted probes includes detection and quantification of a label associated with or incorporated into the extracted probes, wherein the label is selected from a radioactive label, a chemiluminescent label or a fluorescent label.

18. A method according to claim 1, wherein said sample is taken from fluids selected from natural water, industrial water, industrial effluent, municipal wastewater, industrial sludge, thermal mud, food liquid or gel, fermentation media, air, gas, aerosol, a sample taken from a building ventilation duct or air conditioning duct, a sample of food solid, a sample of soil, a sample from medical apparatus, or is a human or animal sample selected from blood, urine, vaginal or intestinal flora.

19. A method according to claim 1, wherein said method is used in combination with a process for triggering an alarm in connection with quality, safety and or sanitary monitoring of the product from which said sample has been obtained.

20. A method according to claim 1, wherein said method is used in in vitro diagnosis of an infectious disease.

21. A method according to claim 1, wherein said method is used in the automatic or feedback control of a microbiological process.

22. A method according to claim 1, wherein said method is used in the automatic or feedback control of a process relating to the removal or prevention of the development of microorganisms.

23. A method according to claim 1 wherein said method is applied in the detection of foam formation during the implementation of activated sludge processes and/or the feedback control of a method relating to the removal or prevention of the said foams.

24. A method according to claim 10, wherein the dehydration comprises a series of ethanol solutions of increasing concentrations.

25. A method according to claim 11, wherein the concentration of said denaturing agent is about 0.01%, the concentration of said Tris-HCl is about 0.02 M, and the concentration of said salt about 0.9 M.

26. A method according to claim 11, wherein said denaturing agent is sodium dodecyl sulfate and said salt is sodium chloride.

27. A method according to claim 13, wherein said denaturing agent is sodium dodecyl sulfate and said salt is sodium chloride.

28. A method according to claim 17, wherein said label is fluorescein.

29. A method according to claim 8, wherein said fixation solution contains about 4% paraformaldehyde.

30. A method according to claim 14, wherein said denaturing agent comprises formamide.

* * * * *

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence :
      primer_bind

<400> SEQUENCE: 1
tgcgaccggt catgg                                                    15

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence :
      primer_bind

<400> SEQUENCE: 2
cgccattgta ttacgtgtga                                               20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence :
      primer_bind

<400> SEQUENCE: 3
gacgggcggt gtgtacaa                                                 18

<210> SEQ ID NO 4
```

-continued

```
<211> LENGTH: 18
<212> TYPE: DNA
<213> ORGANISM: Artificial Sequence
<220> FEATURE:
<223> OTHER INFORMATION: Description of Artificial Sequence :
      primer_bind

<400> SEQUENCE: 4
gctgcctccc gtaggagt                                              18
```